(12) United States Patent
Hotier et al.

(10) Patent No.: US 7,569,141 B2
(45) Date of Patent: Aug. 4, 2009

(54) PROCESS AND DEVICE FOR SIMULATED MOVING BED SEPARATION WITH A REDUCED NUMBER OF LARGE DIAMETER VALVES AND A REDUCED LINE VOLUME

(75) Inventors: Gerard Hotier, Rueil Malmaison (FR); Philibert Leflaive, Mions (FR); Sylvain Louret, Lyons (FR); Frederic Augier, Saint Symphorien D Ozon (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 12/044,306

(22) Filed: Mar. 7, 2008

(65) Prior Publication Data

US 2008/0217232 A1 Sep. 11, 2008

(30) Foreign Application Priority Data

Mar. 9, 2007 (FR) .................................. 07 01773

(51) Int. Cl.
*B01D 15/08* (2006.01)
(52) U.S. Cl. .................................. 210/198.2; 210/659
(58) Field of Classification Search ................. 210/635, 210/656, 659, 662, 198.2
See application file for complete search history.

(56) References Cited

U.S. PATENT DOCUMENTS

| 5,705,061 | A | * | 1/1998 | Moran | ...................... | 210/198.2 |
| 5,882,523 | A | * | 3/1999 | Hotier et al. | ................. | 210/659 |
| 5,972,224 | A |   | 10/1999 | Hotier et al. | | |
| 6,017,448 | A | * | 1/2000 | Hotier et al. | ............. | 210/198.2 |
| 6,093,317 | A | * | 7/2000 | Capelle et al. | ........... | 210/198.2 |
| 6,146,537 | A | * | 11/2000 | Ferschneider et al. | ....... | 210/659 |
| 6,156,197 | A | * | 12/2000 | Dessapt et al. | ........... | 210/198.2 |
| 6,224,762 | B1 | * | 5/2001 | Ferschneider et al. | .... | 210/198.2 |
| 6,261,458 | B1 |   | 7/2001 | Callebert et al. | | |

(Continued)

FOREIGN PATENT DOCUMENTS

DE 199 35 162 A1 2/2000

(Continued)

*Primary Examiner*—Ernest G Therkorn
(74) *Attorney, Agent, or Firm*—Millen, White, Zelano & Branigan, P.C.

(57) ABSTRACT

The invention concerns a simulated moving bed adsorption separation device comprising a limited number of large diameter valves. According to the invention, the device comprises a column with a plurality of sectors Sk with 2 superimposed plates Pi with a single distribution network, each sector Sk comprising an external principal bypass line Lk connected to each plate Pi of Sk via a large diameter plate valve Vi and an external secondary bypass line Mk comprising a small diameter valve VMk connected to the adjacent sector Sk−1. Each line Lk comprises a flow rate limitation means and is connected to each fluid network via a single large diameter valve. Further, the connectors of lines Lk onto the column are offset by at most 20° inside Sk to limit the volume of lines Lk, and are offset by a mean angle in the range 70° to 110° between two neighbouring sectors Sk and Sk+1 so as not to weaken the column mechanically. The plates preferably comprise panels DMEi,j with parallel segments the direction of which varies from plate to plate or per group of 2 plates.

The invention also concerns a separation process using said device.

FIG. 2 to be published.

10 Claims, 7 Drawing Sheets

U.S. PATENT DOCUMENTS

| | | | |
|---|---|---|---|
| 6,402,959 B1 * | 6/2002 | Dessapt et al. | 210/656 |
| 6,454,948 B2 * | 9/2002 | Ferschneider et al. | 210/659 |
| 6,537,451 B1 * | 3/2003 | Hotier | 210/198.2 |
| 6,797,175 B2 * | 9/2004 | Hotier | 210/659 |
| 2001/0008220 A1 * | 7/2001 | Ferschneider et al. | 210/634 |
| 2003/0127394 A1 | 7/2003 | Hotier | |
| 2005/0269268 A1 * | 12/2005 | Hotier | 210/659 |
| 2006/0006113 A1 * | 1/2006 | Couenne et al. | 210/659 |
| 2008/0041788 A1 * | 2/2008 | Hotier et al. | 210/659 |
| 2008/0121586 A1 * | 5/2008 | Hotier et al. | 210/659 |
| 2008/0237132 A1 * | 10/2008 | Hotier et al. | 210/659 |

FOREIGN PATENT DOCUMENTS

| | | |
|---|---|---|
| EP | 1 325 772 A1 | 7/2003 |
| FR | 2 782 657 A1 | 3/2000 |
| FR | 2 794 663 A1 | 12/2000 |

* cited by examiner

PROCESS AND DEVICE FOR SIMULATED MOVING BED SEPARATION WITH A REDUCED NUMBER OF LARGE DIAMETER VALVES AND A REDUCED LINE VOLUME

FIELD OF THE INVENTION

The invention relates to the field of separation of natural or chemical products which are difficult to separate by distillation. A family of processes and associated devices are used which are known as "chromatographic" or "simulated moving bed" or "simulated counter-current" or "simulated co-current" processes or separation devices which we shall hereinafter term "SMB".

A non-exclusive list of the fields concerned is:
the separation of normal paraffins from branched paraffins, naphthenes and aromatics;
olefin/paraffin separation;
the separation of para-xylene from other isomers of C8 aromatics;
the separation of meta-xylene from other isomers of C8 aromatics;
the separation of ethylbenzene from other isomers of C8 aromatics.

Beyond the refinery, and petrochemicals plant, there are many other applications, including glucose/fructose separation, the separation of positional isomers of cresol, optical isomers, etc.

PRIOR ART

SMB chromatographic separation is well known in the art. In general, a simulated moving bed comprises at least three chromatographic zones, advantageously four, five or six zones, each of said zones being constituted by at least one bed or a portion of a column and included between two successive supply or withdrawal points. Typically, at least one feed F to be fractionated and a desorbant D (sometimes termed the eluent) are supplied and at least one raffinate R and extract E are withdrawn. Occasionally, an extract-rich reflux RE is also supplied. It is also possible to use not only a raffinate R but two raffinates R1 and R2. Thus, there are generally 4, 5 or 6 process fluids which are supplied or withdrawn sequentially. The supply and withdrawal points are modified over time, typically shifted in the direction of flow towards the bottom of a bed in a synchronous manner.

A plurality of advantageous variations can improve the function of that type of unit by making asynchronous permutations. Put simply, such asynchronous permutations act to compensate for the dead volume(s) of the recirculation pump(s), as indicated in U.S. Pat. No. 5,578,215, to work with a constant recycle rate on the recirculation pump to eliminate jerky flow rates and pressure, as indicated in U.S. Pat. No. 5,762,806, or finally to operate with at least two chromatographic zones each one of which is equivalent to a non-integral number of adsorbant beds. This latter variation, as indicated in U.S. Pat. Nos. 6,136,198, 6,375,839, 6,712,973 and U.S. Pat. No. 6,413,419, is known as Varicol®. Naturally, these three variations may be combined.

It should be noted that a multi-way rotary valve placing the incoming and outgoing fluids in communication with the beds disposed in the adsorption column or columns only allows a synchronous type permutation. For asynchronous permutations, a plurality of on-off valves is vital. This technical aspect is described below.

The prior art describes in detail various devices and processes which can carry out the separation of feeds in a simulated moving bed. Particular patents which may be cited are U.S. Pat. Nos. 2,985,589, 3,214,247, 3,268,605, 3,592,612, 4,614,204, 4,378,292, 5,200,075 and 5,316,821. These patents also provide details of the function of a SMB.

SMB devices typically comprise at least one column (and frequently two), adsorbant beds Ai disposed in that column, separated by plates Pi with chamber(s) Ci for distribution and/or extraction of fluids into or from the various beds of adsorbant, and controlled means for sequential distribution and extraction of fluids.

Each plate Pi typically comprises a plurality of distributor-mixer-extractor panels or "DMEi,j" supplied via lines or "distribution/extraction manifolds". The plates may be of any type and any geometry, in particular with panels forming adjacent segments of the column section, for example panels with angular segments such as those shown in FIG. 8 of U.S. Pat. No. 6,537,451, which are supplied symmetrically (manifold), or parallel segments such as cutouts in a circumference, as indicated in published U.S. Ser. No. 03/0,127,394, which are supplied bi-symmetrically. Preferably, the separation column comprises parallel segment type DMEi,j plates and bi-symmetrical supplies. Preferably again, the adsorbant is dense packed. This means that a larger quantity of adsorbant can be used in a given column and increases the purity of the desired product and/or the SMB flow rate.

Distribution over each bed requires flux from the preceding bed principal fluid moving along the principal axis of the column) to be collected, the possibility of injecting therein an auxiliary fluid or secondary fluid while mixing the two fluids to the best possible extent, or the possibility of removing part of the collected fluid, extracting it to send it out of the device and also to re-distribute a fluid onto the next bed.

To this end, it is possible to use in a plate Pi chambers Ci,k for distribution (injection/extraction) which may be separate or be common with the mixing chambers. Plates Pi with one or more chambers are known, either supplied (or exhausted) separately by different fluids at a given time, or supplied (or exhausted) simultaneously and in parallel by the same fluid at a given time. In the first case, the plate is said to have a plurality of distribution networks and in the second case it has a single distribution network. The invention pertains exclusively to a device comprising plates with a single distribution network.

In general, either all of the fluid or principal flux is passed through the column in a manner described in U.S. Pat. No. 2,985,589, or a large part or all of that flux is evacuated as described in the process disclosed in U.S. Pat. No. 5,200,075.

A generic problem with all SMB devices is minimizing the pollution generated by the liquid encountered in the various zones and volumes of the supply and withdrawal circuits for the fluids to/from the plates during modifications to the supply and withdrawal points during operation of the SMB. When during the operating sequence a line, chamber or supply zone for a plate Pi is no longer flushed by a process fluid, it becomes a dead zone in which the liquid stagnates, and only moves again when another process fluid moves in it. Since the nature of SMB requires that this is a different process fluid, the liquid in the dead zone is necessarily displaced by a liquid with a substantially different composition. Mixing or circulation over a short time interval of fluids with substantially different compositions thus introduces a deviation from ideal operation, which proscribes discontinuities in composition.

A further problem may reside in any re-circulation between different zones of the same plate, which thus also induces a deviation from ideal operation.

To overcome these problems linked to re-circulation and dead zones, various techniques are already known in the prior art:

a) flushing of the lines and dead zones by a desorbant or relatively pure desired product has already been proposed. That technique effectively prevents pollution of the desired product during its extraction. However, since the flushing liquid typically has a composition which is very different from the liquid it displaces, this introduces discontinuities in the composition which are prejudicial to ideal operation. This first flushing variation typically carries out "short duration flushes at a high concentration gradient". These flushes are brief to limit composition discontinuity effects.

b) As described in U.S. Pat. No. 5,972,224, another solution consists of passing the majority of the principal flux towards the interior of a column and a minority of that flow towards the exterior, typically 2% to 20% of the flux, via external bypass lines between neighbouring plates. This flush is typically carried out most of the time or continuously, so that the lines and zones are no longer "dead" but are flushed. Such a system with flushing via bypass lines is shown in FIG. 1 of U.S. Pat. No. 5,972,224 and repeated in a simplified version in FIG. 1 of the present application. Since the bypass lines are designed for a low flow rate, they may as a result be small in diameter, and comprise a small diameter valve, which reduces the cost of the system.

A first advantage of such a system is that the injection and withdrawal circuits for the secondary fluids are flushed with liquid with a composition which is very close to the displaced liquid since firstly, the bypass derives from a neighbouring plate, and secondly, flushing is substantially continuous rather than discontinuous. Further, the flow rates in the bypasses are preferably determined so that the transit rate in each bypass is substantially the same as the rate of advance of the concentration gradient in the principal flux of the SMB. Hence, the various lines and capacities are flushed with a fluid which has a composition which is substantially identical to that of the liquid which is found therein, and the liquid circulating in a bypass is re-introduced at a point where the composition of the principal flux is substantially identical. This second variation can thus carry out "long duration flushes with a small or zero concentration gradient".

A second advantage of this long duration flush system (apart from the injection or withdrawal periods) is that it can remove the effects of possible re-circulation between zones of the same plate due to small pressure drop differences.

Regarding the function of a SMB, the controlled fluid distribution and extraction means of a SMB are typically one of the two following major types of technique:

either, for each plate, a plurality of controlled on-off valves for supplying or withdrawing fluids, said valves typically being located in the immediate vicinity of the corresponding plate, and in particular comprising, for each plate Pi, at least 4 controlled two-way on-off valves respectively to supply fluids F and D and withdraw fluids E and R;

or a multi-way rotary valve for supplying or withdrawing fluids over the whole assembly.

The first technique uses two-way valves, which can be mass produced, resulting in increased reliability and a relatively low unit cost. The second technique uses only a single valve, but that single valve is a multi-way valve (more than two pathways) and necessarily is of special construction, of large dimensions and is extremely complex. Further, this second technology excludes the possibility of asynchronous permutations, as in the Varicol device.

The invention concerns SMB using conventional two-way valves, i.e. using the first of the two techniques described above. In particular, it concerns an improved device for simulated moving bed separation comprising a plurality of two-way valves, with a slightly reduced number of controlled valves, and in particular with a substantially reduced number of large opening diameter controlled valves, compared with the prior art. It can be used both for SMB with synchronous permutations and for SMB with asynchronous permutations, for example a Varicol.

BRIEF DESCRIPTION OF THE INVENTION

The invention concerns an improved device for simulated moving bed separation belonging to the major simulated moving bed technique using a plurality of controlled valves (on-off or creeper valves), typically standard valves which are mass produced at low cost to the required high standard (seal/reliability).

One of the essential aims of the invention is to reduce the relative disadvantage of this type of SMB, which is to require a large number of controlled large diameter two-way valves, i.e. with an opening diameter compatible with the movement of SMB process fluids at their nominal flow rate. Typically, the invention can substantially reduce the number of large opening diameter controlled valves while preserving the advantage of being able to use effective flushing of dead zones of the "long duration with a small or zero concentration gradient" type.

A further aim of the invention is to provide a device which requires a reduced number of two-way large (opening) diameter valves without the open/close frequency of those valves being increased with respect to the prior art; this along with the reduced number of large diameter valves limits the statistical risks of malfunction and thus increases the reliability of the system.

Further, in a preferred variation of the device, the number of large diameter valves which allow circulation of the principal fluids of the SMB at their nominal flow rate can be further reduced.

The device of the invention may be used in new facilities, but is also compatible with various existing facilities on which it may be installed, by carrying out limited modifications. It is also compatible with various types and geometries of plates Pi, for example plates with angular sector panels or with parallel segments, provided that these plates (or the majority thereof) are of the single distribution network type, for the sequential supply or withdrawal of a SMB process fluid.

Thus, a means has been discovered which can substantially reduce the number of principal large diameter controlled valves, corresponding to the sequential inlets/outlets for fluids for the SMB process at their nominal flow rate: in the prior art, for each plate there is at least one set of 4 principal network valves for supply/withdrawal of F, D, R, E. This number is further increased if there are more than 4 process fluids for the SMB, for example if there are two raffinates R1, R2 or if a reflux RE is used which is rich in the desired product typically extract. Thus, there are as many large diameter controlled valves per plate as there are process fluids for the SMB, i.e. usually between 4 and 6, limits included.

In the prior art, the bypass lines are only small diameter auxiliary lines which are not used by the fluids F, D, R, B, (E1), (E2), (RE) at their nominal supply or withdrawal flow rates, but use a substantially smaller flow rate, typically less than 20% of the flow rate circulating in the column, often between 2% and 10% of that flow rate. Thus, they typically include a controlled creeper valve (to control the flush rate) with a small opening diameter (or equivalent diameter with the same cross section of passage).

According to the invention, the column or a principal portion of that column (more than 50% of the height of the column at least) is grouped into superimposed sectors Sk, each sector Sk comprising two successive beds of adsorbant $A_i$, $A_{i+1}$, and 2 plates $P_i$, $P_{i+1}$ located respectively immediately below these beds, and also comprising a principal bypass line Lk. In contrast to the prior art, the fluids of the SMB use the bypass line Lk at their nominal flow rate (and not simply by a small flush flow) and a single set of principal network valves (sequential supply or withdrawal) per column sector (for two plates and not per plate as in the prior art) is used, these large diameter valves being connected to the bypass line Lk to allow circulation of these fluids via Lk.

In accordance with the invention, "plate valves" are also provided, i.e. a large diameter valve, respectively $V_i$ or $V_{i+1}$, for each of plates $P_i$, $P_{i+1}$ of Sk, as well as additional means for limiting the small flows of flushing fluid moving in Lk.

In accordance with the invention, a secondary bypass line Mk connecting sector Sk to the immediately lower sector Sk+1 is provided. This provides an excellent flush of all of the plates of the SMB and tends to improve the purity of the recovered product, typically the extract.

As will be described below, in particular with respect to the description of FIG. 2, which will provide a clearer picture of the invention, the total number of large diameter controlled valves is reduced.

Finally, according to a characteristic disposition of the device of the invention, the connections of lines Lk on the column are offset by at most 20° within Sk, to limit the volume of lines Lk, and offset by a mean angle in the range 70° to 110° between two neighbouring sectors Sk and Sk+1 so as not to render the column mechanically weak. The plates preferably comprise panels $DME_{i,j}$ with parallel segments the direction of which varies from plate to plate or per group of 2 plates.

The invention also concerns a process for SMB separation using the device described above, in particular for the separation of an aromatic, in particular para-xylene or meta-xylene, from a feed of aromatic hydrocarbons containing 8 carbon atoms.

The invention also concerns a process for SMB separation using the device described above, in particular for separating a normal-paraffin hydrocarbon or an olefinic hydrocarbon from a cut including such a hydrocarbon.

DETAILED DESCRIPTION OF THE INVENTION

The invention will be better understood from the following description, made with reference to FIG. 1 (prior art) and FIGS. 2 to 7 (device or parts of the device of the invention).

To achieve one of the aforementioned aims, the invention thus proposes a device for separating at least one desired compound from a mixture comprising that compound by simulated moving bed adsorption comprising:

at least one column comprising a plurality of adsorbant beds $A_i$ separated by distributor/extractor plates $P_i$ to sequentially supply and extract at least two supply fluids: a feed F and a desorbant D, and at least two withdrawn fluids: a raffinate R and an extract E, $P_i$ being disposed between the bed $A_i$ and the immediately inferior bed $A_{i+1}$;

the device also comprising at least one feed network F-Net, a desorbant network D-Net, a raffinate network R-Net and an extract network E-Net, each of said networks being connected to the column via a plurality of lines comprising controlled two-way isolating valves with an opening diameter of a or above, termed network valves, for sequential supply or withdrawal of said supply or withdrawal fluids;

in which the column is divided, over at least the major part of its height, into a plurality of adjacent superimposed sections Sk, each sector Sk being essentially constituted by 2 successive adsorbant beds $A_i$, $A_{i+1}$ and by the 2 distributor/extractor plates $P_i$, $P_{i+1}$ which are respectively disposed immediately below $A_i$ and $A_{i+1}$ (i.e. exactly 2 beds and 2 plates as well as the corresponding shell section);

each of the distributor/extractor plates $P_i$, $P_{i+1}$ of each of the sectors Sk has a single common network for sequential supply and withdrawal of F, D, R, E;

plates $P_i$, $P_{i+1}$ of each sector Sk are connected together via an external principal bypass line Lk connected to each of plates $P_i$, $P_{i+1}$ of Sk via a connector comprising a single two-way controlled isolating valve which belongs to said plate $P_i$ or $P_{i+1}$, termed a plate valve $V_i$ or $V_{i+1}$, with an opening diameter which is greater than or equal to the value a for sequential supply or withdrawal of said supply or withdrawal fluids in or from $P_i$;

each of said bypass lines Lk comprises at least one controlled means for limiting the flow moving in Lk, which is either installed on the line Lk or bypasses a plate valve $V_i$ or $V_{i+1}$ of a plate of Sk;

in which the bypass line Lk of each of the sectors Sk is connected to each of the networks F-Net, D-Net, R-Net, E-Net via a single line with an internal diameter of a or more comprising a single network valve, respectively VFk, VDk, VRk, VEk, which has an opening diameter of a or more, for sequential supply or withdrawal of fluid corresponding to F, D, R or E to or from the sector Sk under consideration;

the device also comprising a plurality of external secondary bypass lines Mk, each of lines Mk connecting the 2 adjacent sectors Sk+1 and Sk via 2 connecting points;

the first connecting point being disposed on the connector connected to the lower plate $P_{i-1}$ of the upper sector Sk−1 between $P_{i-1}$ and the plate valve $V_{i-1}$;

the second connecting point being disposed on the connector connected to the upper plate $P_i$ of the lower sector Sk between $P_i$ and the plate valve $V_i$;

each of the external secondary bypass lines Mk comprising a controlled two-way valve VMk with an internal opening diameter of β or less, in which $\beta \leq 0.6\alpha$;

this device comprising at least 2 adjacent superimposed sectors Sk and Sk+1 each with two distributor/extractor plates, Sk comprising plates $P_{i-1}$ and $P_i$ connected by a principal external bypass line Lk connected to the column via two connectors respectively comprising the valves of plates $V_i$ and $V_{i+1}$, and Sk+1 comprising plates $P_{i+1}$ and $P_{i+2}$ connected by an external bypass line Lk+1 connected to the column via two connectors respectively comprising plate valves $V_{i+2}$ and $V_{i+3}$; in which the two connectors of Sk onto the column have between them an angular offset with respect to the axis of the column which is zero or 20° or less, the two connectors of Sk+1 onto the column having between them an angular offset with respect to the axis of the column which is zero or 20° or less, and the connectors of Sk having a mean angular offset in the range 70° to 110° with respect to the connectors of Sk+1.

Typically, α and β are selected so as to satisfy the following inequality: 30 mm ≦ 1.7×β ≦ α ≦ 600 mm. It will be seen that valves VMk with an internal opening diameter of β or less are much smaller and cheaper than valves with an internal opening diameter of α or more.

In contrast to the prior art device, the device of the invention enables the bypass line Lk to be used to circulate fluids F, D, R, E (and preferably any other process fluids) supplied to the SMB and withdrawn from the SMB at a sector Sk, via a single set of corresponding network valves, instead of a set of network valves per plate Pi as in the prior art. This allows a reduction in the overall number of controlled large diameter valves, even when taking into account the addition of supplemental valves, namely plate valves Vi, as will be shown below in the description of FIGS. 2 and 3.

The controlled valves cited above: network valves and plate valves Vi, are typically high quality valves (reliability, seal, service life) carrying out the sequential operation of the SMB.

More generally, all of the controlled valves ensuring the sequential function of the SMB: network valves, plate valves Vi, and also the valves of the controlled means for limiting the flow circulating in Lk, must be considered, in accordance with the invention, as the "principal" valves of the SMB, connected to the column and controlled via the system for controlling the sequential function of the SMB (computer, programmable means or other equivalent system).

Certain principal valves for the sequential operation of the SMB were mentioned above as being unique to the invention: Vi for each plate Pi; a single set of network valves VFk, VDk, VRk, VEk etc for each sector Sk. These valves are exclusively those allowing the sequential function of the SMB. However, the scope of the invention encompasses the additional use of other valves such as occasional secondary isolation valves, typically of a far inferior quality, which may or may not be controlled, but which do not participate in the sequential operation of the SMB and, for example, being present for the purposes of dismantling any equipment: pump or principal valve used for sequential operation, etc.

Typically, in the device of the invention, the bypass line Lk, which is used to transmit all of the fluids F, D, R, E etc at their nominal flow rate is no longer a small auxiliary line as in the prior art, but generally has an internal diameter which is at least equal to the largest opening diameter of the network valves connected to Lk to allow the fluids F, D, R, E to circulate at their nominal flow rate without limiting capacity. The nominal flow rate of a process fluid is by definition the controlled flow rate of this fluid, which is used during the sequential operation of the SMB for the desired separation.

Because bypass lines Lk are used which can transport large flows, controlled flow rate limitation means are advantageously also used to circulate a small flow as a bypass in Lk (typically 2% to 20% of the flow moving in the column). The term "bypass circulation" as used here means that a (small) fraction of the flow moving in the column is withdrawn from a plate and re-introduced into another plate of the same sector Sk. The term "controlled means" typically applies to a controlled valve, typically programmed by a link, starting from information provided by a flow meter.

To this end, a flow rate regulating valve may be used which is installed directly on the line Lk, as shown in FIG. 3. This valve is thus typically a creeper valve and not an on-off controlled valve (which has only 2 possible positions: fully open, and closed).

However, in a preferred variation of the invention, shown in FIG. 2, at least one or preferably each of the bypass lines Lk comprises a controlled means for limiting the flow circulating in Lk, which is not installed directly on Lk but as a bypass around a plate valve of a plate of Sk, for example around the plate valve Vi+1 of the lower plate Pi+1. This flow rate limitation means, disposed on a small secondary bypass lk, also generally comprises a controlled valve vi+1 with a smaller diameter opening than that of Vi+1, for example with an opening diameter at most 60% or 50% that of Vi+1, for example in the range 10% to 50% of the opening diameter of Vi+1.

The valve vi+1 typically has an opening diameter of β or less and often less than or equal to half of α. The dimension of this flush rate control valve is advantageously the same as that of the valve VMk disposed on Mk. In both cases, a limited flush flow rate is thus regulated. Thus, in the same manner, each of the secondary bypass lines Mk typically comprises at least one means for controlling the flow moving in Mk, said means including the valve VMk.

When an internal flush is to be carried out as a bypass via Lk and this internal bypass flow is to be limited (typically circulating from the upper plate Pi of Sk to the lower plate Pi+1 of Sk), plate valve Vi remains closed, the small valve vi+1 bypassing around Vi+1 is opened, this valve controlling the flow rate, and Vi is opened to circulate a limited flow from Pi and recycled to Pi+1 via Lk and lk (see FIG. 2).

Thus, the use of a small secondary bypass lk allows a smaller opening diameter valve to be used than if the flow limitation means were installed on the principal bypass line Lk, which has a relatively larger diameter because Lk must allow circulation of fluids F, D, R, E at their nominal flow rate.

According to the invention, the connector comprising Vi+1 must be interpreted as not including the small secondary bypass lk around Vi+1, nor the small valve vi+1 disposed on lk. This connector thus comprises a single valve Vi+1 allowing circulation of the principal fluids F, D, R, E, etc.

The device of the invention can also limit the lengths of the external bypass lines Lk and Lk+1 since the connecting connectors (or taps, a connector also being a tap onto the column) of each of these lines are superimposed or have a small angular offset (at most 20°). This is favourable as regards limiting the internal volumes of lines which have to be flushed when the supply/extraction fluid is changed. However, due to a large mean angular offset in the range 70° to 110° between the connectors of two adjacent superimposed sectors Sk and Sk+1, mechanical weakening of the column by an accumulation of substantially superimposed taps on the same generatrix of the column is avoided.

In accordance with the invention, the term "orientation" of a connector or tap applies to the orientated straight line starting from the centre of the plate on the axis of the column and directed towards this connector (at its point of connection with the column). By definition, the angular offset between two connector orientations (for two different plates) is the smallest angle formed by the orientations of the connectors of these two plates, projected onto the horizontal reference plane. It is thus an angle which is always in the range [0°-180°]. The mean orientation of two connectors (for an assembly of two different plates) having an angular offset of an angle alpha of <180°, is by definition the median orientation corresponding to an angular offset of alpha/2 with respect to two orientations of the connectors under consideration. The mean angular offset between the connectors of two sectors Sk and Sk+1 is the angular offset of the mean orientations of the connectors of these two sectors.

Typically, the whole column with the exception of the head of the column comprising the head plate and optionally the column bottom comprising the lower bed and/or lower plate is constituted by a plurality of superimposed 2-plate sectors in which the two connectors of the same sector Sk has an angular offset with respect to the axis of the column of zero or 20° or less, and any two superimposed adjacent sectors have between them a mean angular offset of their connectors in the range 70° to 110°.

The lower plate may also belong to a sector Sk with a connection of Lk at the lower point to the column outlet line (and no longer to the column) and thus preferably has the same angular offset characteristics between its two taps (zero or 20° or less) as well as a mean angular offset of these taps with respect to those of the immediately superior sector Sk−1 which is typically in the range 70° to 110°.

In this case, in accordance with the invention the lower outlet line from the column bottom is assimilated with a plate Pn corresponding to the lower adsorbant bed An. In fact, typically there is no plate Pn below the adsorbant bed An disposed at the column bottom as there is no need to distribute the fluids into the immediately inferior bed. In addition, in accordance with the invention, in this case it is assumed that the missing plate Pn is replaced by the lower outlet line from the column, typically connected either to the inlet to the same column, via a recirculation pump or to the head of a second separation column.

Preferably, the connectors of any sector Sk have between them a substantially zero angular offset and any two adjacent superimposed sectors have between them a mean angular offset of their connectors of substantially 90°. In this case, the bypass lines Lk are typically parallel to one generatrix of the column and thus of minimum length.

In accordance with a preferred characteristic of the invention, plates formed by panels DMEi,j with parallel segments are used, as shown in FIGS. 4a and 4b; advantageously, the angular offsets of the taps are used to change the orientation of these parallel segment panels DMEi,j.

This change of direction of the parallel segment panels (or panel orientation) can limit local heterogeneities of fluid circulation due to the geometry of the plates and their supply/extraction system: by avoiding a uniform orientation of the panels, and in contrast by changing their orientation, preferably by an angle close to 90°, a cumulative effect of circulation heterogeneities along the column is avoided. As an example, a smaller circulation at a local zone of a plate will be partially or totally compensated for by an increased zone of circulation of a lower plate located in the same portion of the column. This tends to equalize the adsorption fronts of products on a section of the column.

In accordance with the invention, the terms "panels" or "segments" will be used equally.

In accordance with the invention, the term "direction of the parallel segments" applies to the straight line, not orientated in one or the other direction, located in a horizontal reference plane which is parallel to the sectors under consideration and passes through the column axis.

By definition, the angular offset between two directions (or orientations) of parallel segment panels (of two different plates) is the smallest angle formed by the directions of the parallel segments of these two plates, projected onto the same horizontal reference plane. It is thus an angle which is always included in the interval [0°-90°].

The mean direction (or orientation) of the parallel segments of two different plates wherein one of the directions is offset by an angle alpha of <90° with respect to the other is by definition the median direction, corresponding to an offset angle of alpha/2 with respect to the two directions under consideration.

Thus, in accordance with a first design variation of the plates of the device, each plate Pi of a sector Sk is subdivided into a plurality of panels DMEi,j with sectors parallel to a direction connected to a single connector (EMi) to supply the supply fluids and withdraw the extraction fluids and for each plate of a sector Sk, the directions of the parallel segment panels of the plates of a single sector Sk have an angular offset of zero or 20° or less, and the mean direction of the panels with parallel segment panels of a sector Sk has an angular offset in the range 70° to 90°, limits included, with respect to that of the panels of a neighbouring sector Sk+1 or Sk−1.

The direction of the parallel segments of this plate preferably have a constant angular offset with the connector connected to this plate, this constant offset typically being either substantially zero or substantially 90°.

In accordance with this variation, the direction of the panels DMEi,j with parallel segments of the plates of a single sector Sk are thus substantially similar or identical (with at most 20° of offset). In contrast, the mean directions of the parallel segment panels of the plates change by an angle in the range 70° to 90° when passing from one sector Sk to an adjacent sector. Thus, every two plates there is a large change in direction (close to 90°) of panels, every 2 plates (sector by sector).

In a second variation in the design of the plates and device, each plate Pi of a sector Sk is subdivided into a plurality of segments parallel to one direction, connected to a single connector to supply the supply fluids and extract the withdrawn fluids and for each assembly of two superimposed adjacent plates belonging to the same sector Sk or to two superimposed sectors, the direction of the parallel segment panels of one of the two plates has an angular offset in the range 70° to 90°, limits included, with the direction of the parallel segments of the other plate.

In this variation, the directions of the parallel segments of the two plates of a single sector Sk are substantially offset by 90°, and this same offset exists when passing from the plate below Sk to the adjacent lower plate belonging to the lower sector Sk+1. The changes in direction of the parallel segments thus in this case occur at each plate and no longer at each group of 2 plates (at each sector), which increases the changes in direction of the sectors. In contrast, since the 2 connectors have a zero or small angular offset within the same sector, this change in direction then necessitates two different designs of plate, with segment orientations offset by 90°, as will be explained when the Figures are described.

Typically, the bypass line Lk has an internal diameter at least equal to the largest opening diameter of the network valves connected to Lk. Thus, the diameter of Lk does not constitute a limitation to the flow compared to the opening diameter of the network valves connected directly to Lk.

As already mentioned, the SMB may function with a reflux RE, including the extract, or typically rich in the desired product obtained by distilling the extract to eliminate the desorbant (comprising more than 50%, or even 90% or even 99% of the desired product). Preferably, the device of the invention then comprises a sequential supply network RE-Net of the reflux RE, this network being connected to each of the sectors Sk via a single line with an internal diameter of a or more comprising a single network valve REk which has an opening diameter of $\alpha$ or more. Thus, the reflux network is connected in a manner identical to those of the other process fluids F, D, R, E.

In analogous manner, the SMB may also function with a sequential withdrawal of a second raffinate R2, and in this case the device of the invention preferably comprises a network R2-Net connected to each of the sectors Sk via a single line with an internal diameter of a or more comprising a single network valve REk which has an opening diameter of a or more. Thus, the second raffinate network is connected in a manner identical to those of the other process fluids F, D, R, E, (RE).

The invention also concerns a process for separating a product using a device as described above. Typically, during a cycle.

each line Lk is used sequentially to circulate F, D, R, E at their nominal flow rate and optionally a reflux RE and/or a second raffinate R2 to or from each plate of Sk via the corresponding plate valve and the corresponding network valve in series;

a flush is carried out at a flow rate which is lower than that of the nominal flow rates of fluids F, D, R, E and optionally RE and/or R2, of each of the principal external bypass lines Lk during at least part of the time in which no network valve connected to Lk is open, using an internal stream deriving from a plate of the device and recycled to another plate of the device, and all internal flushing of Lk is stopped when a network valve connected to Lk is open;

a flush is carried out at a flow rate which is lower than that of the nominal flow rates of fluids F, D, R, E of each of the external secondary bypass lines Mk for at least part of the time, using an internal stream deriving from a plate of the device and recycled to another plate of the device.

The process of the invention thus uses the SMB device by efficiently carrying out flushes by circulation from plate to plate via external bypass lines Lk and Mk. Typically, Lk is flushed by circulating a stream from an upper plate Pi of Sk, recycled to the lower plate Pi+1 of Sk.

Typically again, Mk is flushed by circulating a stream derived from a lower plate Pi−1 of Sk−1, recycled to the upper plate Pi of Sk.

In general, an internal flush of Lk is carried out from an upper plate Pi of Sk to a lower plate Pi+1 of Sk, in any period when Sk is not connected to one of said sequential supply or sequential withdrawal network fluids and which is immediately prior to a period in which one of the network valves connected to Sk is open to supply or withdraw one of said fluids to or from the upper plate Pi. This internal flush results in opening Vi in the period preceding a period for supply to or withdrawal from the plate Pi (which also requires opening Vi) and avoids opening or closing of Vi between these consecutive periods. The reduction in the number of movements of valves reduces wear on those valves and increases the reliability of the device and the associated process.

Internal flushes of at least two and typically all of the bypass lines Lk is carried out. In general, for a given line Lk (or Mk), the internal flush lasts at least 20%, often at least 40% or even at least 50% of the time.

Preferably, for each of the bypass lines Lk, Lk is flushed during the whole period of time in which no network valve connected to Lk is open.

Typically, Lk is used by each of fluids F, D, R, E over the whole of its length during a cycle. This prevents the appearance of any dead zones in Lk.

The plate valves Vi+1 and Vi of the connectors connected via an external secondary bypass line Mk are preferably closed when Mk is flushed. This avoids partial mixing of the flush flow with the fluid present in Lk.

Mk may be flushed during the whole period in which the plate valves Vi−1 and Vi of the connectors connected via the secondary external bypass line Mk are closed.

In a variation of the process of the invention, asynchronous permutations of the supply and withdrawal points for fluids F, D, R, E in the column are carried out.

It is also possible to use the device with chromatographic zones at least some of which are equivalent to a non integral number of adsorbant beds, typically a Varicol.

The invention is not limited to a particular separation but may be used for any simulated moving bed separation. As an example, it is possible to carry out a process for separating an aromatic hydrocarbon, for example para-xylene or meta-xylene, from an aromatic feed essentially containing 8 carbon atoms and comprising that hydrocarbon.

It is also possible to carry out a process for separating at least one normal-paraffin hydrocarbon from a feed of hydrocarbons comprising such a hydrocarbon or a process for separating at least one olefinic hydrocarbon from a feed of hydrocarbons comprising such a hydrocarbon.

DESCRIPTION OF FIGURES AND OPERATION OF DEVICES SHOWN

The invention will be readily understood from the accompanying drawings and description in which:

FIG. 1 is a diagrammatic representation of part of a prior art SMB device, with the corresponding network valves;

FIG. 2 diagrammatically shows part of a SMB device of the invention, comprising three superimposed sections Sk, Sk+1, Sk+2 with the corresponding principal bypasses, secondary bypasses, network valves, plate valves and flow rate limitation valves;

FIG. 3 diagrammatically shows part of a SMB device of the invention, comprising flow rate limitation valves located on lines Lk, Lk+1;

Figure 1:
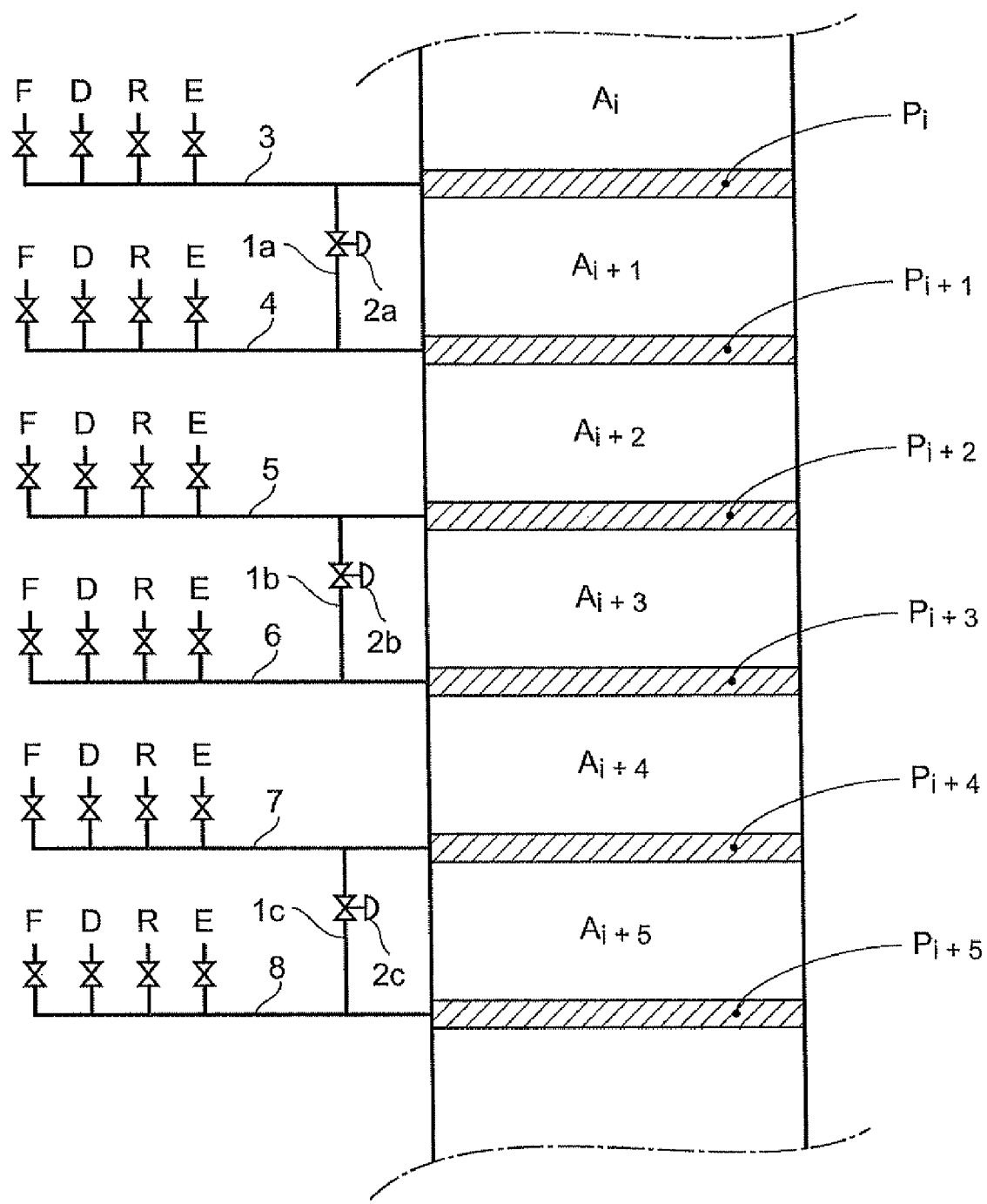

We refer now to FIG. 1, representing part of a chromatographic column of a prior art SMB. Each of the beds of adsorbant, Ai, Ai+1, Ai+2, Ai+3, Ai+4 Ai+5 is disposed above a plate Pi, Pi+1, Pi+2, Pi+3, Pi+4, Pi+5 and each of said plates is connected via a line, respectively 3, 4, 5, 6, 7, 8, to each of 4 fluid networks F, D, R, E via a valve (no reference). There are thus 4 principal valves per plate. Further, the plates are connected in pairs via a bypass line 1a, 1b, 1c, typically with a relatively small diameter and comprising a valve with a relatively small diameter ($\beta$ or less), respectively 2a, 2b, 2c, to allow the passage of a limited bypass flow: 2% to 20% of the flow circulating in the column.

In total, then, for each plate Pi, there are 4 principal valves with a relatively large opening diameter of a value of $\alpha$ or more >$\beta$ (compatible with the nominal flow rates of F, D, R, E) and on average 0.5 small diameter valves (one for 2 plates) giving an average of 4.5 valves per plate, including four with a large opening diameter of $\alpha$ or more.

The function of a SMB using such a column is well known to the skilled person. Typically, valve 2a, 2b or 2c of a bypass line is open and regulates a limited flush flow when no fluid F, D, R, E is supplied to or withdrawn from one of the 2 plates connected via the bypass line (bypass temporarily in service). In contrast, valve 2a, or 2b, or 2c of a bypass line is closed when one of fluids F, D, R, E is supplied to or withdrawn from one of the 2 plates connected via the bypass line (bypass temporarily out of service).

Figure 2:
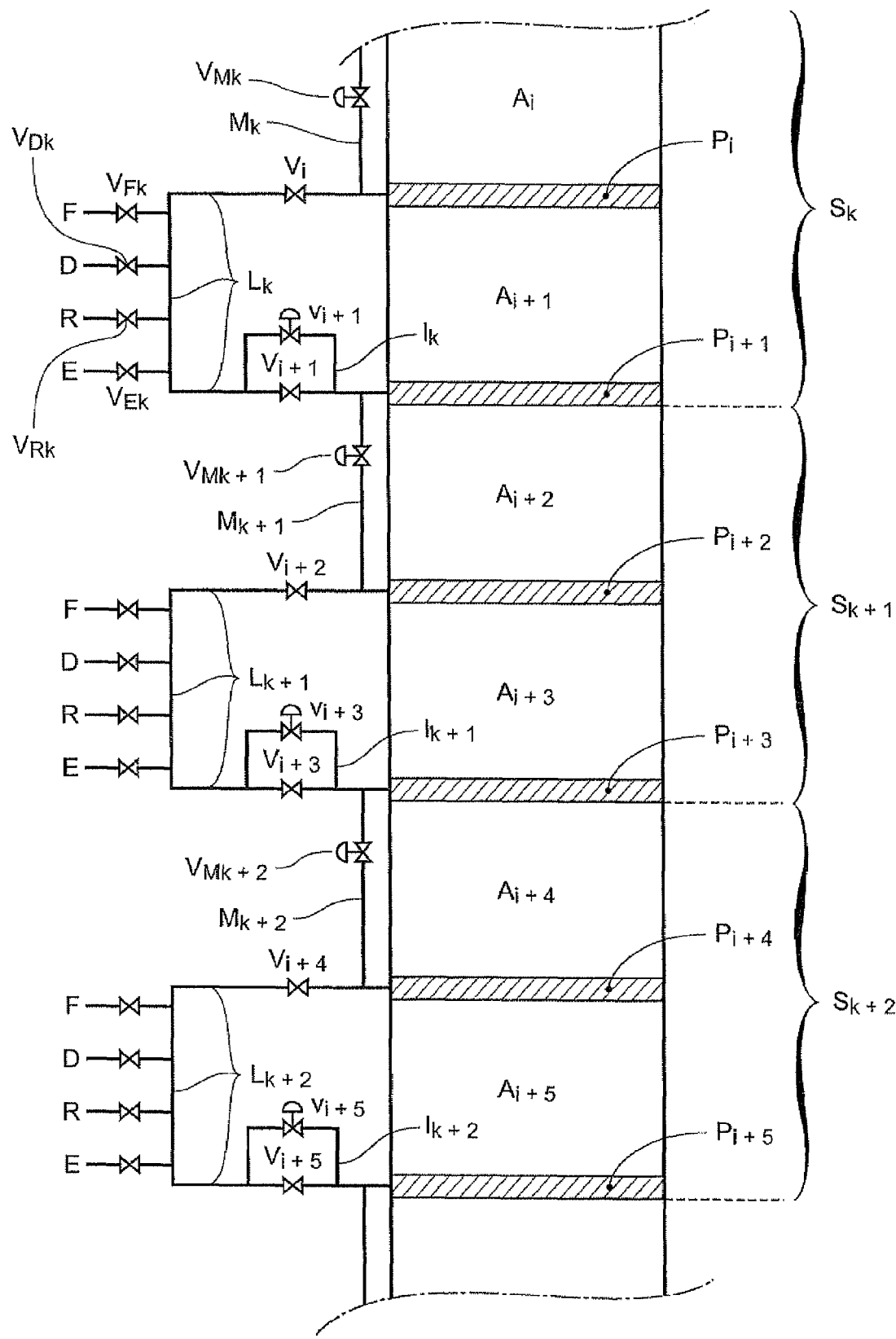

FIG. 2 shows part of a column of a device of the invention comprising 3 sectors Sk, Sk+1, Sk+2, each comprising 2 beds of adsorbant and 2 plates located immediately below. The 2 plates of each sector are connected via a principal bypass line, with a relatively large diameter, typically a or larger, respectively Lk, Lk+1, Lk+2, which is suitable for circulation of fluids F, D, R, E etc at their nominal flow rate. Each bypass line is connected to a set of 4 network valves with a relatively large opening diameter of a or more for sequential supply and withdrawal of process fluids. In contrast to the prior art, this set of 4 valves supplies not 1 but 2 plates.

Thus, for the first sector Sk, there are 4 network valves VFk, VDk, VRk, VEk supplying both Pi and Pi+1.

Each plate is also connected to a corresponding bypass line Lk or Lk+1 or Lk+2 via a connector (corresponding to the horizontal part of the line in the figure) comprising a single two-way controlled isolation valve belonging to the plate, termed a plate valve: Vi, Vi+1, Vi+2, Vi+3, Vi+4, Vi+5. Each lower plate valve of a sector: Vi+1, Vi+3, Vi+5 also has a small secondary bypass line lk, lk+1, lk+2 provided with a valve which is typically of small diameter: vi+1, vi+3, vi+5.

Each plate is also connected to a secondary bypass line Mk or Mk+1 or Mk+2 provided with a relatively small diameter valve VMk or VMk+1 or VMk+2.

In total, for each sector of 2 plates, there are 4 relatively large diameter network valves, 2 plate valves also with a relatively large diameter to allow the circulation of F, D, R, E etc at their nominal flow rate, and two relatively small diameter bypass valves (auxiliary and secondary), namely 8 valves, giving an average of 4 valves per plate, including 3 large diameter valves. Thus, one large diameter valve per plate is gained when this device is compared with prior art FIG. 1.

The device operates as follows:

For the sector Sk, for example, when in a given period, one of the fluids F, D, R, E is to be supplied to or withdrawn from the plate Pi, the corresponding network valve VFk, VDk, VRk, VEk is opened as well as the plate valve Vi. The other network valves of the sector Sk are then closed, as well as Vi+1 and the small secondary bypass valve VMk of the upper secondary bypass line Mk and the small auxiliary bypass valve vi+1. In contrast, the small secondary bypass valve VMk+1 of the secondary bypass line Mk+1 is preferably open.

When in another period one of fluids F, D, R, E are to be supplied to or withdrawn from plate Pi+1, the corresponding network valve VFk, VDk, VRk or VEk and the plate valve Vi+1 are opened. The other network valves of Sk are then closed, as well as Vi. The small auxiliary bypass valve vi+1 may remain closed. The small secondary bypass valve VMk of the upper secondary bypass line Mk is preferably open and the small secondary bypass valve VMk+1 of the secondary bypass line Mk+1 is necessarily closed.

When in a third period one of fluids F, D, R, E is not to be supplied to or withdrawn from plates Pi and Pi+1, the network valves VFk, VDk, VRk and VEk are closed. Next, a limited bypass flow is circulated in the line Lk (withdrawn from Pi and injected into Pi+1) by opening Vi, closing Vi+1 and opening the small auxiliary bypass valve vi+1. Thus, a small bypass flow vi+1 is ensured via lk is ensured which is typically a regulating valve (progressive opening) controlled by regulating the flow rate from a flow meter, not shown.

When in a fourth period, 1) one of fluids F, D, R, E is neither to be supplied to nor withdrawn from plates Pi and Pi+1, network valves VFk, VDk, VRk, VEk are closed, and 2) a zero bypass flow is required in the line Lk, Vi, Vi+1 and the small auxiliary bypass valve vi+1 are closed. A limited bypass flow is then circulated at a limited flow rate in the secondary bypass line Mk and optionally in Mk+1 except when the plates Pi−1 or Pi+2 are in the supply or withdrawal phase, in which case the corresponding secondary bypass line must remain out of service.

The other sectors Sk+1, Sk+2 function in an analogous manner.

One example of a type of function of a sector Sk is as follows, in which the valves for the function of Sk which are open are mentioned and the valves which are not mentioned are closed. Only the movements in the secondary bypass in Mk for flushing Pi are described (not those in Mk+1)

Period 1: bypass flush from Pi to Pi+1. Open valves: Vi, vi+1;

Period 2: injection of desorbant into Pi. Open valves: Vi, VDk;

Period 3: injection of desorbant into Pi+1. Open valves: Vi+1, VDk, and bypass flush from Pi−1 to Pi. Open valve: VMk;

Period 4: bypass flush from Pi to Pi+1. Open valves: Vi, vi+1;

Period 5: withdrawal of raffinate from Pi. Open valves: Vi, VRk;

Period 6: withdrawal of raffinate from Pi+1. Open valves: Vi+1, VRk. And bypass flush from Pi−1 to Pi. Open valve: VMk;

Period 7: bypass flush from Pi to Pi+1. Open valves: Vi, vi+1;

Period 8: bypass flush from Pi−1 to Pi. Open valve: VMk;

Period 9: bypass flush from Pi to Pi+1. Open valves: Vi, vi+1;

Period 10: bypass flush from Pi−1 to Pi. Open valve: VMk;

Period 11: bypass flush from Pi to Pi+1. Open valves: Vi, vi+1;

Period 12: injection of feed into Pi. Open valves: Vi, VFk;

Period 13: injection of feed into Pi+1. Open valves: Vi+1, VFk. And bypass flush from Pi−1 to Pi. Open valve: VMk;

Period 14: bypass flush from Pi to Pi+1. Open valves: Vi, vi+1;

Period 15: bypass flush from Pi−1 to Pi. Open valves: VMk;

Period 16: bypass flush from Pi to Pi+1. Open valves: Vi, vi+1;

Period 17: bypass flush from Pi−1 to Pi. Open valves: VMk;

Period 18: bypass flush from Pi to Pi+1. Open valves: Vi, vi+1;

Period 19: bypass flush from Pi−1 to Pi. Open valves: VMk;

Period 20: bypass flush from Pi to Pi+1. Open valves: Vi, vi+1;

Period 21: withdrawal of extract from Pi. Open valves: Vi, VLk;

Period 22: withdrawal of extract from Pi+1. Open valves: Vi+1, VEk. And bypass flush from Pi+1 to Pi. Open valve: VMk;

Period 23: bypass flush from Pi to Pi+1. Open valves: Vi, vi+1;

Period 24: bypass flush from Pi−1 to Pi. Open valves: VMk.

The principles which allow the preferred sequencing are as follows:

1) each time one of the principal fluids (F, D, R, E) is withdrawn or injected using a network valve in a bypass line Lk, this network valve remains open two times in succession (during the successive 2 periods). The first time, the upper, open plate valve allows connection to the upper plate Pi, and the lower plate valve Vi+1 as well as the small valve vi+1 controlling the auxiliary bypass fluid of line lk are closed. The second time, the lower plate valve Vi+1 is open, allows connection to the lower plate Pi+1 and the upper plate valve Vi and the small fluid bypass control valve vi+1 are closed. Further, the small control valve VMk of the upper secondary bypass line Mk is open to place in communication the plates Pi−1 (not shown) of sector Sk−1 (not shown) and the plate Pi of the sector Sk.

2) Outside the periods for injection or withdrawal of the principal fluids (F, D, R, E), a bypass flow is alternately circulated in Lk every other time. The upper plate valve Vi is then open, the lower valve Vi+1 is closed and the small control valve vi+1 on the auxiliary bypass around Vi+1 regulates the bypass flow via the auxiliary bypass lk. Alternatively, a bypass flow circulates in the upper secondary bypass line Mk regulated by the small control valve VMk, the two plate valves Vi−1 and Vi being closed to produce a bypass between Pi−1 and Pi. This latter bypass flow would not, however, be brought into service if the plate Pi−1 were supplied to or withdrawn via F, D, R, E etc.

Figure 3:
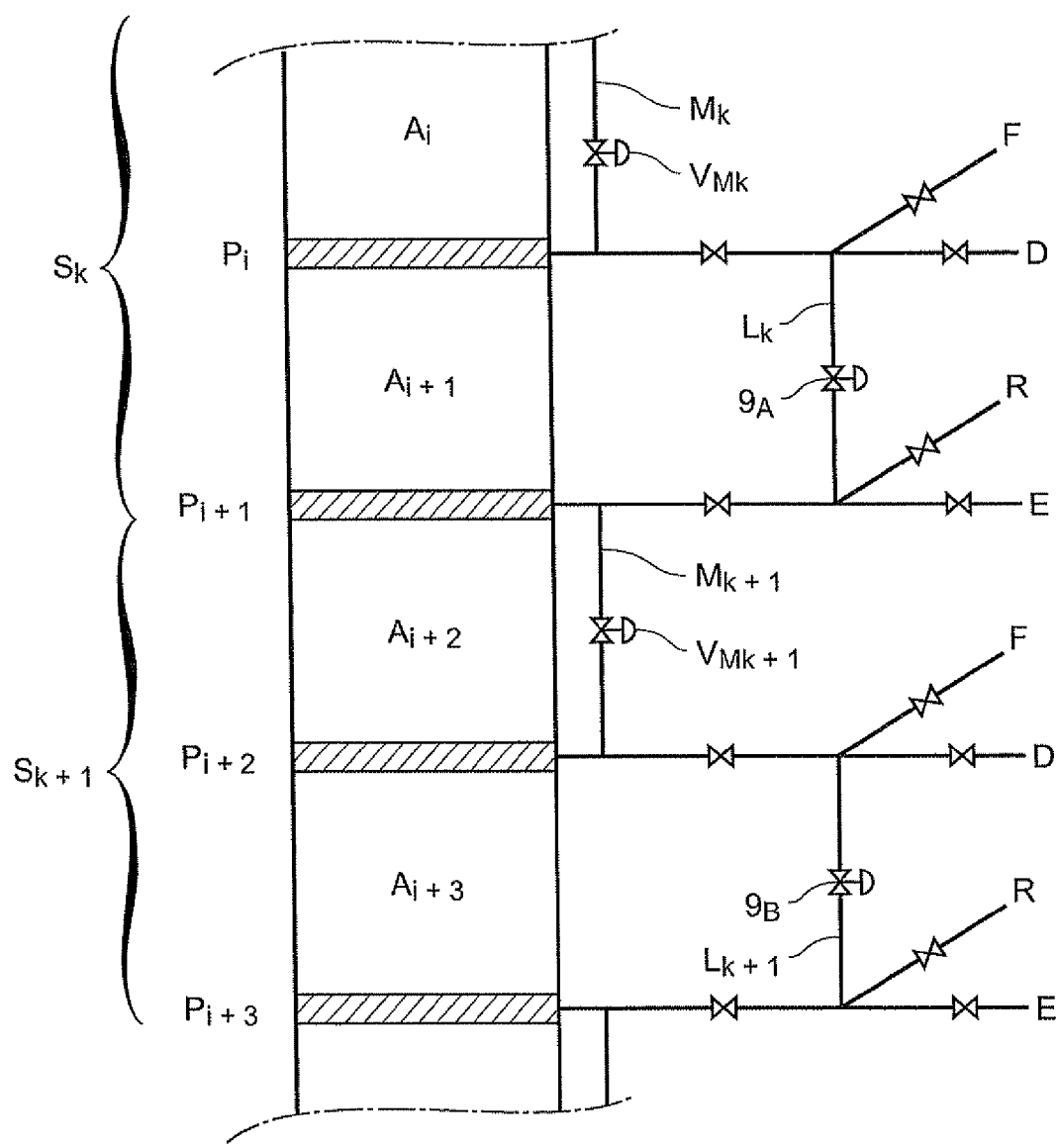

FIG. 3 shows a portion of a column of a SMB in accordance with another embodiment of the invention. The plate valves (not numbered) do not include the small auxiliary bypass line lk to limit the bypass flush flow in Lk, as in the device of FIG. 2. This function is ensured by a valve which typically has a progressive opening: 9A for Lk and 9B for Lk+1. This does not allow the auxiliary lines lk, lk+1 to be used, but requires relatively large diameter valves 9A, 9B so as not to limit the flow circulating in Lk.

Alternatively, a plate valve of Lk may be used as a flow regulating valve instead of the valve 9A and/or the valve 9B. This valve or these valves must thus have an enhanced seal.

FIGS. 4a, 4b, 4c and 4d show top views of various embodiments of a plate Pi with parallel segments panels DMEi,j with their supply/extraction network. The present invention is not concerned with the geometry of the branches of this network.

Figure 4A:
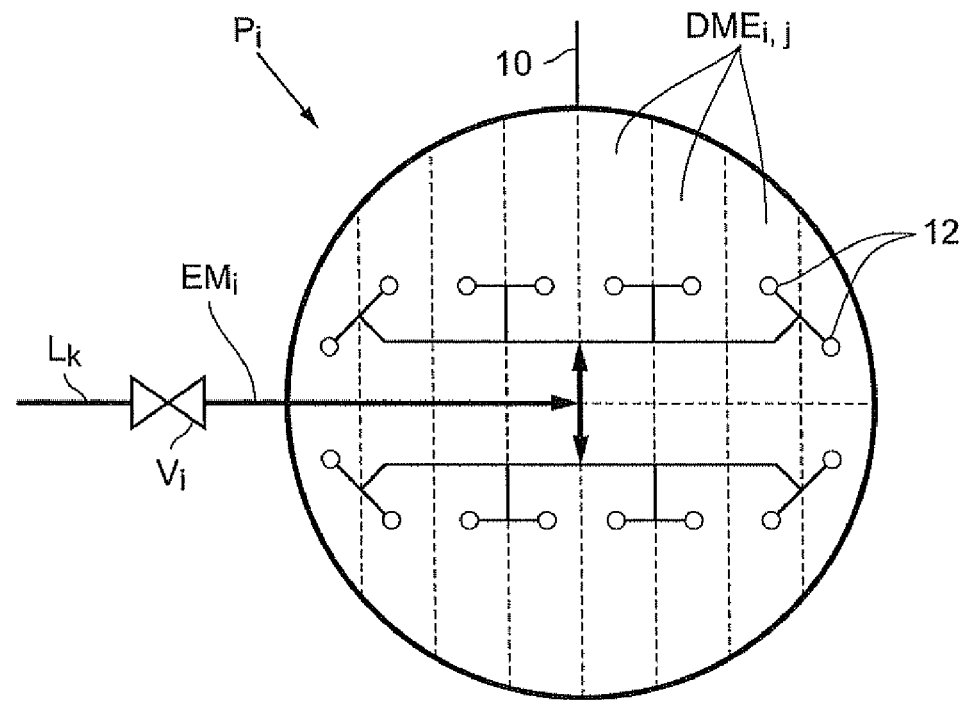
FIGS. 4a, 4b, 4c and 4d show four plate variations Pi with parallel segments with their supply/extraction network.
Figure 4B:
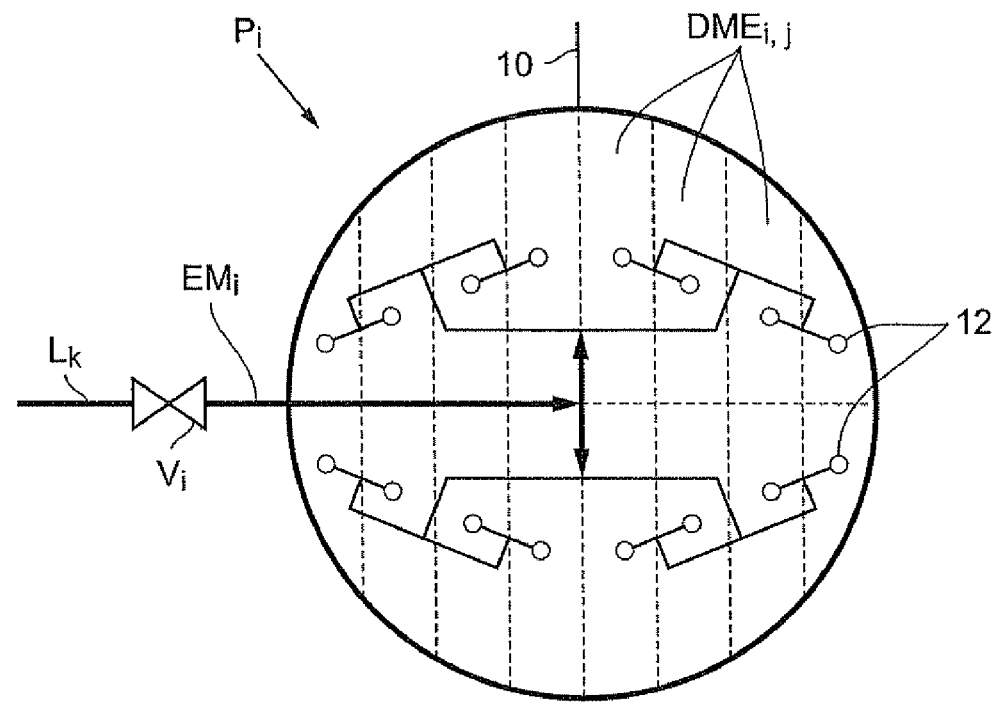
Figure 4C:
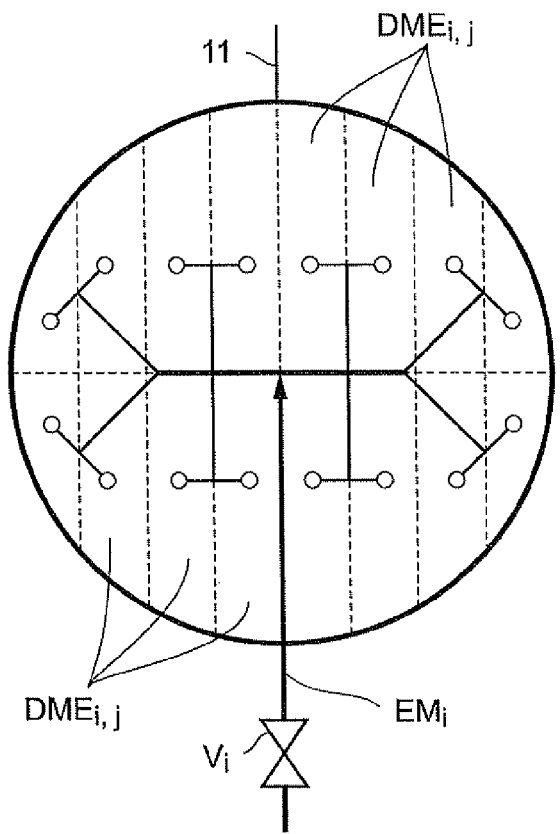

For each of the plates corresponding to FIGS. 4a, 4b and 4c, the single connector EMi connected to the supply/extraction process fluids network enters the column radially to connect, via a radial line, to the centre of the column where a first division into two is carried out. A series of successive subdivisions can individually supply all of the panels DMEi,j to supply and withdraw the SMB fluids in a regular manner over the whole section of the plate.

Figure 4D:
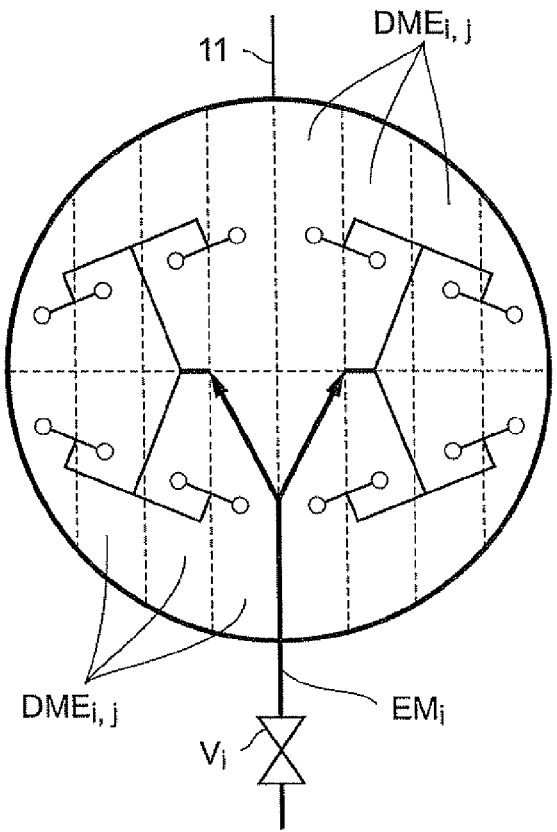

For the plate of FIG. 4d, the radial line is subdivided more upstream and does not pass via the centre of the column, which means that a central strut can be installed to support the plates and the adsorbant bed located above the plate.

For the plates of FIGS. 4a and 4b, the panels DMEi,j extend perpendicular to the connector EMi, parallel to one and the same direction indicated by the non orientated straight line 10. This direction of the parallel segments has an angular offset of 90° with respect to the connector EMi.

In contrast, for the plates of FIGS. 4c and 4d, the panels DMEi,j extend parallel to the connector EMi and to a direction indicated by the non orientated straight line 11. This direction of the parallel segments thus has a zero angular offset with respect to the connector EMi.

The branches of the single common network for sequential supply and withdrawal of the process fluids can be carried out in a variety of manners. The networks of the plates of FIGS. 4a and 4c comprise both divisions into two, for example upstream of the terminal ends 12 for connection to the panels, and also the raked subdivisions.

The network of plates of FIGS. 4b and 4d exclusively comprise successive divisions into two. It is also possible to use divisions such as those disclosed in U.S. Pat. No. 5,938,333.

In general, the dimensions of the lines decreases with the branches, but it is also possible to have parts of the network with lines with the same diameter, and divisions into two with a reduction in diameter on one or two downstream branches, etc. The scope of the invention also encompasses supplying each panel DMEi,j via two terminal ends 12 rather than just one.

Figure 5A:
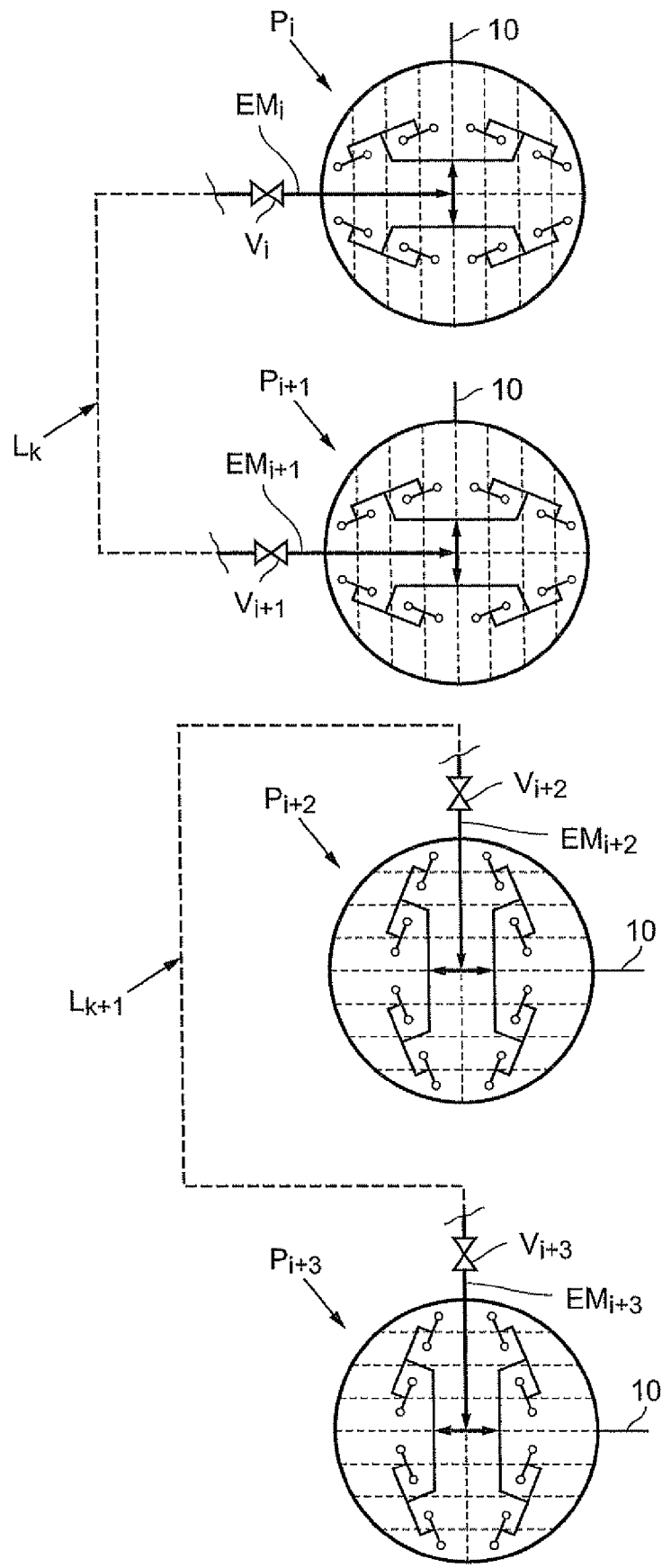
FIGS. 5a and 5b show two variations in the disposition of 4 successive adjacent plates corresponding to two sectors Sk and Sk+1.

FIG. 5a shows a first variation in the disposition of 4 adjacent superimposed plates corresponding to two sectors Sk and Sk+1. In this variation, all the plates have the design of FIG. 4b, all of the parallel segment panels DMEi,j of one plate being perpendicular to the single connector EMi corresponding to this plate, and thus having an angular offset of 90° with this connector.

The connectors of plates Pi−1 and Pi belonging to the same sector Sk are superimposed and thus have an angular offset of zero. For this reason, the line Lk shown as a dotted line is typically of minimum length and is easy to install as it does not have to wind around the column.

The connectors of plates Pi+1 and Pi+2 belonging to the same immediately inferior sector Sk+1 are also superimposed and thus also have a zero angular offset. For this reason, the line Lk+1 shown in dotted lines is also typically of minimum length and is easy to install as it does not have to wind around the column.

The connectors of Sk+1 are, in contrast, offset by 90° with respect to those of Sk. This is also the case for the directions of the parallel segment panels of the plates of Sk+1 which are offset by 90° with respect to those of the plates of Sk. Thus, there is an angular offset of 90° of the parallel segments, of every two plates, i.e. sector by sector. This disposition can avoid or limit the accumulation of fluid circulation heterogeneities in the column section because of the imperfectly homogeneous nature of the supply/extraction system. It tends to regularize the adsorption fronts in the various points of the column section compared with a disposition with all of the plates directly superimposed, resulting in an accumulation of heterogeneities due to each new plate.

The variation in the disposition of the 4 adjacent superimposed (neighbouring) plates of FIG. 5a can thus produce both a typically minimum length for the bypass lines Lk, Lk+1 which is easy to install, but also avoid or limit the accumulation of circulation heterogeneities in the column. Finally, it can avoid an accumulation of taps on one generatrix of the column, the connectors being offset by 90° at each new sector. This is favorable for the mechanical behaviour of the column, which is not weakened.

Figure 5B:
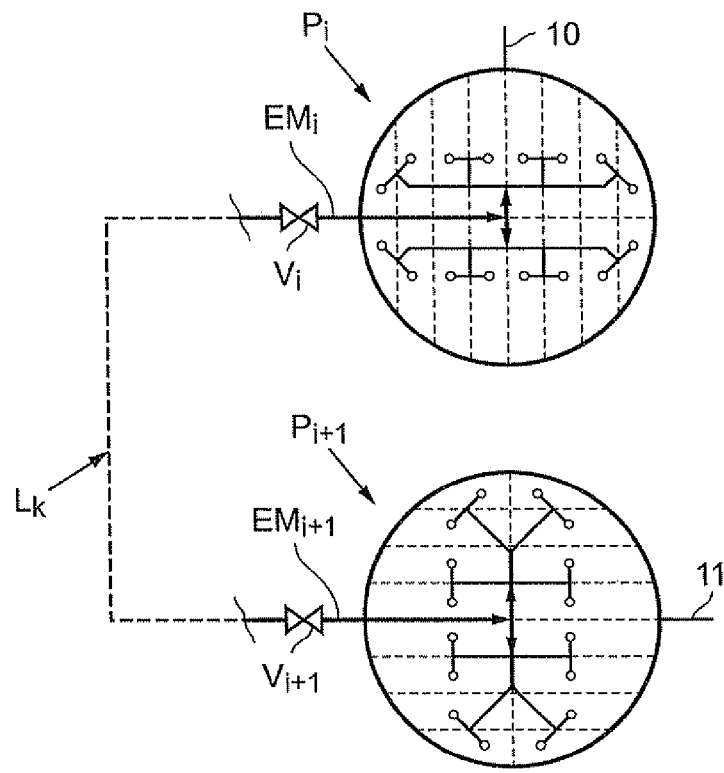
Figure 5B:
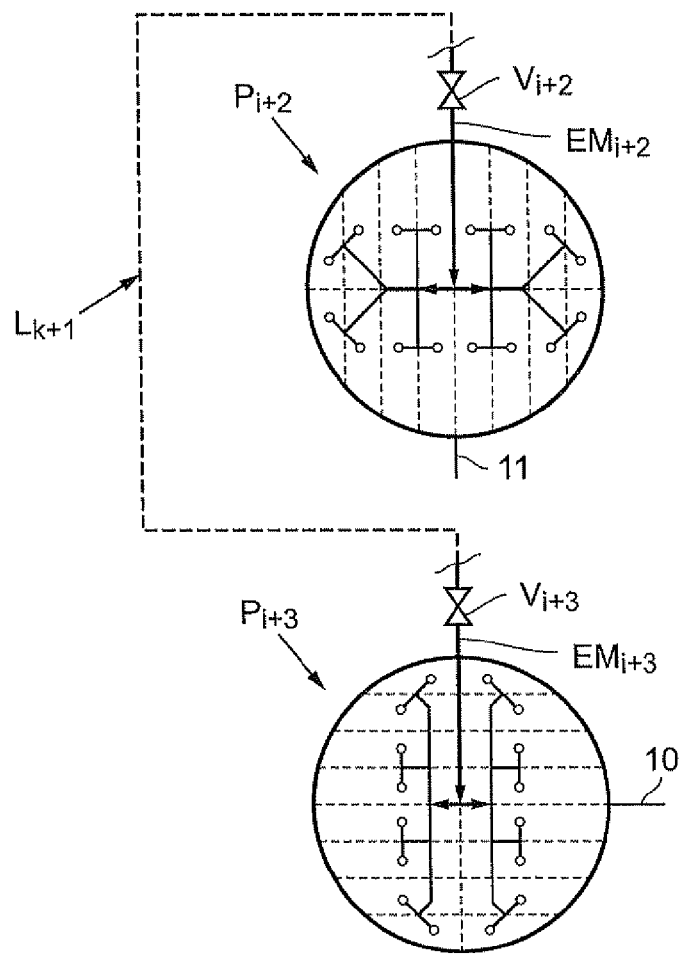

FIG. 5b shows another variation in the disposition of 4 successive adjacent plates corresponding to two sectors Sk and Sk+1. In this variation, there is an angular offset of 90° in the direction of the parallel segment panels of a plate to that of the parallel segment panels of one or the adjacent plate (closest plate(s)), i.e. plate by plate and not sector by sector. This further augments the limitation in the accumulation of circulation heterogeneities in the column.

The two connectors (taps) of one sector Sk or Sk+1 remain superimposed to preserve the advantage of bypass lines typically with a minimum length, and easy to install. This is achieved by the alternating use of two types of plates with different distribution networks: one type in accordance with the design of FIG. 4a (for Pi and Pi+3) and one type in accordance with the design of FIG. 4c (for Pi+1 and Pi+2).

This variation thus allows a more frequent alternation of plates with the change in orientation of the parallel segments, in contrast to using 2 different types of plates. It preserves the advantage of bypass lines which are typically of minimum length and which are easy to install.

Best Implementation

The best implementation of the invention is a SMB wherein the column or columns are essentially constituted by sectors Sk with small valves vi+1 etc in the auxiliary bypass of plates Pi+1 etc as seen in FIG. 2.

In such a device, there are 3 large diameter valves per plate (6 per sector Sk: VFk, VDk, VRk, VEk, Vi, Vi+1) as opposed to 4 in the prior art (see FIG. 1). On average there is one small regulating valve per plate (VMk and vi+1 for the 2 plates of Sk) as opposed to 0.5 in the prior art, but this valve is much cheaper and the total number of valves is reduced (4 as opposed to 4.5).

The plates of the preferred embodiment of the device and their parallel segments are offset in pairs by 90° (sector by sector, without changing the plate geometry) as shown in FIG. 5a, or are offset one by one by 90° (late by plate, with a change in plate geometry), as shown in FIG. 5b, which regularizes the flow of fluids in the column and reduces the volume of the principal external bypass lines Lk which do not need to wind about the column, without weakening the column by an accumulation of superimposed taps (connectors).

The device of the invention as described may be used for any process for chromatographic separation, in particular to separate an aromatic hydrocarbon from a feed of aromatic hydrocarbons essentially containing 8 carbon atoms and including that hydrocarbon.

In particular, it may be used to separate para-xylene from an aromatic cut essentially composed of C8 hydrocarbons, using toluene or para-diethylbenzene as a desorbant and a zeolite as an adsorbant as described, for example, in FR-2 789 914. It may also be used to separate meta-xylene from an aromatic C8 cut, using toluene or tetraline as a desorbant and an adsorbant such as that described in U.S. Pat. No. 5,900,523 and patent applications FR-05/52.485 and FR-05/52.486.

It may also be used to separate one or more normal paraffins (separated from the remainder of the hydrocarbons) from a mixture of hydrocarbons, in particular paraffinic or paraffinic and naphthenic, for example using normal butane or normal pentane as the desorbant (optionally isooctane as in inert diluent) and a 4a zeolite as the adsorbant.

Finally, it may be used to separate at least one olefin from a hydrocarbon cut comprising such a hydrocarbon, under conditions known in the art, for example using an X zeolite exchanged with calcium.

The invention is not limited to the above description and to carry it out, the skilled person is at liberty to employ any other characteristic technique which is known in the art.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The preceding examples can be repeated with similar success by substituting the generically or specifically described reactants and/or operating conditions of this invention for those used in the preceding examples.

The entire disclosures of all applications, patents and publications, cited herein and of corresponding French application Ser. No. 07/01.773, filed Mar. 9, 2007 are incorporated by reference herein.

From the foregoing description, one skilled in the art can easily ascertain the essential characteristics of this invention and, without departing from the spirit and scope thereof can make various changes and modifications of the invention to adapt it to various usages and conditions.

The invention claimed is:

1. A device which can separate at least one compound from a mixture comprising said compound by simulated moving bed adsorption, comprising:

at least one column comprising a plurality of adsorbant beds Ai separated by distributor/extractor plates Pi for sequential supply and extraction of at least two supply fluids: a feed F and a desorbant D, and at least two withdrawal fluids: a raffinate R and an extract E, Pi being disposed between the bed Ai and the immediately lower bed Ai+1;

the device also comprising at least one feed network F-Net, a desorbant network D-Net, a raffinate network R-Net and an extract network E-Net, each of said networks being connected to the column via a plurality of lines comprising controlled two-way isolating valves with an opening diameter of α or above, termed network valves, for sequential supply or withdrawal of said supply or withdrawal fluids;

in which the column is divided, over at least the major part of its height, into a plurality of adjacent superimposed sections Sk, each sector Sk being constituted by a column section essentially comprising by 2 successive adsorbant beds Ai, Ai+1 and by the 2 distributor/extractor plates Pi, Pi+1 which are respectively disposed immediately below Ai and Ai+1;

each of the distributor/extractor plates Pi, Pi+1 of each of the sectors Sk has a single common network for sequential supply and withdrawal of F, D, R, E;

plates Pi, Pi+1 of each sector Sk are connected together via an external principal bypass line Lk connected to each of plates Pi, Pi+1 of Sk via a connector comprising a single two-way controlled isolating valve which belongs to said plate Pi or Pi+1, termed a plate valve Vi or Vi+1, with an opening diameter which is greater than or equal to the value α for sequential supply or withdrawal of said supply or withdrawal fluids into or from Pi;

each of said bypass lines Lk comprises at least one controlled means for limiting the flow moving in Lk, which is either installed on the line Lk or bypasses a plate valve Vi or Vi+1 of a plate of Sk;

in which the bypass line Lk of each of the sectors Sk is connected to each of the networks F-Net, D-Net, R-Net, E-Net via a single line with an internal diameter of α or more comprising a single network valve, respectively VFk, VDk, VRk, VEk, which has an opening diameter of α or more, for sequential supply or withdrawal of fluid corresponding to F, D, R or E to or from the sector Sk under consideration;

the device also comprising a plurality of external secondary bypass lines Mk, each of lines Mk connecting the 2 adjacent sectors Sk−1 and Sk via 2 connecting points;

the first connecting point being disposed on the connector connecting the lower plate Pi−1 of the upper sector Sk−1 between Pi−1 and the plate valve Vi−1;

the second connecting point being disposed on the connector connecting the upper plate Pi of the lower sector Sk between Pi and the plate valve Vi;

each of the external secondary bypass lines Mk comprising a controlled two-way valve VMk with an internal opening diameter of β or less, in which $\beta \leq 0.6\alpha$;

said device comprising at least two superimposed adjacent sectors Sk and Sk+1, each with two distributor/extractor plates, Sk comprising the plates Pi and Pi+1 connected via an external bypass line Lk connected to the column via two connectors respectively comprising the plate valves Vi and Vi+1, and Sk+1 comprising the plates Pi+2 and Pi+3 connected via an external bypass line Lk+1 connected to the column via two connectors respectively comprising the plate valves Vi+2 and Vi+3, in which the two connectors of Sk on the column have between them an angular offset with respect to the axis of the column which is zero or 20° or less, the two connectors of Sk+1 on the column have between them an angular offset with respect to the axis of the column which is zero or 20° or less, and the connectors of Sk have with the connectors of Sk+1 a mean angular offset in the range 70° to 110°.

2. A device according to claim 1, in which the whole column, with the exception of the column head comprising the head plate and optionally the column bottom comprising the lower bed and/or the lower plate, is constituted by a plurality of superimposed sectors of two plates, in which the two connectors of a single sector Sk have between them an angular offset with respect to the axis of the column of zero or 20° or less, and any two adjacent superimposed sectors have between them a mean angular offset of their connectors in the range 70° to 110°.

3. A device according to claim 2, in which the connectors of any sector Sk have between them an angular offset of substantially zero, and any two adjacent superimposed sectors have between them a mean angular offset of their connectors of substantially 90°.

4. A device according to claim 1, in which each plate Pi of a sector Sk is subdivided into a plurality of panels DMEi,j with segments parallel to one direction connected to a single connector (EMi) to supply the supply fluids and extract withdrawal fluids and in which for each plate of a sector Sk, the directions of the parallel segment panels of the plates of a single sector Sk have between them an angular offset of zero or 20° or less, and the mean direction of the parallel segment panels of the plates of a sector Sk has an angular offset in the range 70° to 90°, limits included, with respect to that of the panels of a neighbouring sector Sk+1 or Sk−1.

5. A device according to claim 1, in which each plate Pi of a sector Sk is subdivided into a plurality of panels DMEi,j with segments parallel to one direction, connected to a single connector (EMi) for supply of supply fluids and extraction of withdrawal fluids, in which for each assembly of two superimposed adjacent plates belonging to a single sector Sk or to two superimposed sectors, the direction of the parallel segments of one of the plates has an angular offset in the range 70° to 90°, limits included, with the direction of the parallel segments of the other plate.

6. A device according to claim 1, in which the bypass line Lk has an internal diameter equal to at least the largest opening diameter of the network valves connected to Lk.

7. A device according to claim 1, in which the whole column with the possible exception of the column head comprising the head plate is constituted by said adjacent superimposed sectors Sk, the column comprising a lower outlet line assimilated to a plate Pn corresponding to the lower bed of adsorbant An.

8. A device according to claim 1, in which each of said bypass lines Lk comprises at least one controlled means for limiting the flow circulating in Lk, which is installed as a bypass about a plate valve Vi+1 of a plate Pi of Sk.

9. A device according to claim 8, in which said means for limiting the flow circulating in Lk installed as a bypass around said plate valve Vi+1 comprises a controlled valve with a smaller diameter opening than that of Vi+1.

10. A device according to claim 1, in which 30 mm $\leq 1.7 \times \beta \leq \alpha \leq 600$ mm.

* * * * *